United States Patent [19]
Miller et al.

[11] Patent Number: 5,474,540
[45] Date of Patent: Dec. 12, 1995

[54] FLUID SEPARATION CONTROL ATTACHMENT FOR PHYSIOLOGIC GLUE APPLICATOR

[75] Inventors: Curtis Miller, Eagan; Brian McLevish, St. Paul, both of Minn.

[73] Assignee: Micromedics, Inc., Eagan, Minn.

[21] Appl. No.: 218,352

[22] Filed: Mar. 25, 1994

[51] Int. Cl.$^6$ ............................ A61M 5/00; A61M 37/00
[52] U.S. Cl. ................................ 604/191; 604/82
[58] Field of Search .................. 604/82, 94, 191, 604/198, 187; 222/137, 145; 239/398, 401, 420

[56] References Cited

U.S. PATENT DOCUMENTS

| | | |
|---|---|---|
| 3,179,107 | 4/1965 | Clark . |
| 3,223,083 | 12/1965 | Cobey . |
| 4,040,420 | 8/1977 | Speer . |
| 4,067,333 | 1/1978 | Reinhardt et al. . |
| 4,109,653 | 8/1978 | Kozam et al. . |
| 4,359,049 | 11/1982 | Redl et al. . |
| 4,631,055 | 12/1986 | Redl et al. . |
| 4,734,261 | 3/1988 | Koizumi et al. ........................ 604/191 |
| 4,735,616 | 4/1988 | Eibl et al. . |
| 4,767,416 | 8/1988 | Wolf et al. . |
| 4,842,581 | 6/1989 | Davis . |
| 4,874,368 | 10/1989 | Miller et al. ........................... 604/191 |
| 4,978,336 | 12/1990 | Capozzi et al. . |
| 4,979,942 | 12/1990 | Wolf et al. . |
| 5,104,375 | 4/1992 | Wolf et al. . |
| 5,116,315 | 5/1992 | Capozzi et al. . |
| 5,185,001 | 2/1993 | Galanakis . |
| 5,290,259 | 3/1994 | Fischer ................................... 604/191 |
| 5,328,462 | 7/1994 | Fischer ................................... 604/191 |

Primary Examiner—C. Fred Rosenbaum
Assistant Examiner—Frank Wilkens, III
Attorney, Agent, or Firm—Kinney & Lange

[57] ABSTRACT

A fluid delivery device for delivery and mixing of fibrin glue components at a treatment site during surgery includes a slidable sleeve for controlling interaction of fluid dispensed from a pair of adjacent tubes. A pair of syringes are attached to a fluid separation control attachment which allows the fluids from each of the syringes to be forced into the adjacent tubes. When the fluids exit the free ends of the adjacent tubes, they interact and mix when the slidable sleeve thereon is in one position, but are inhibited from interacting and mixing when the slidable sleeve is in another position.

20 Claims, 5 Drawing Sheets

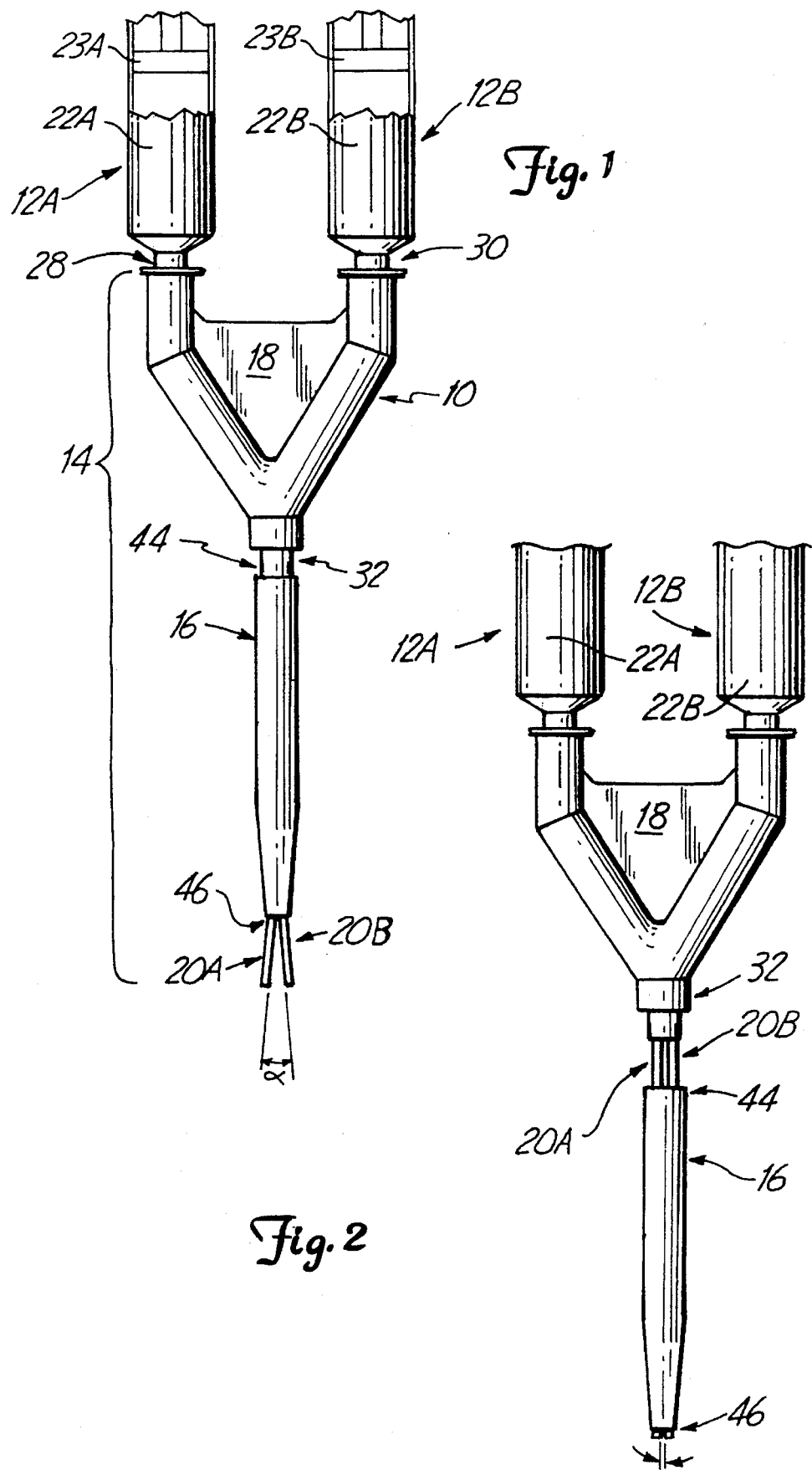

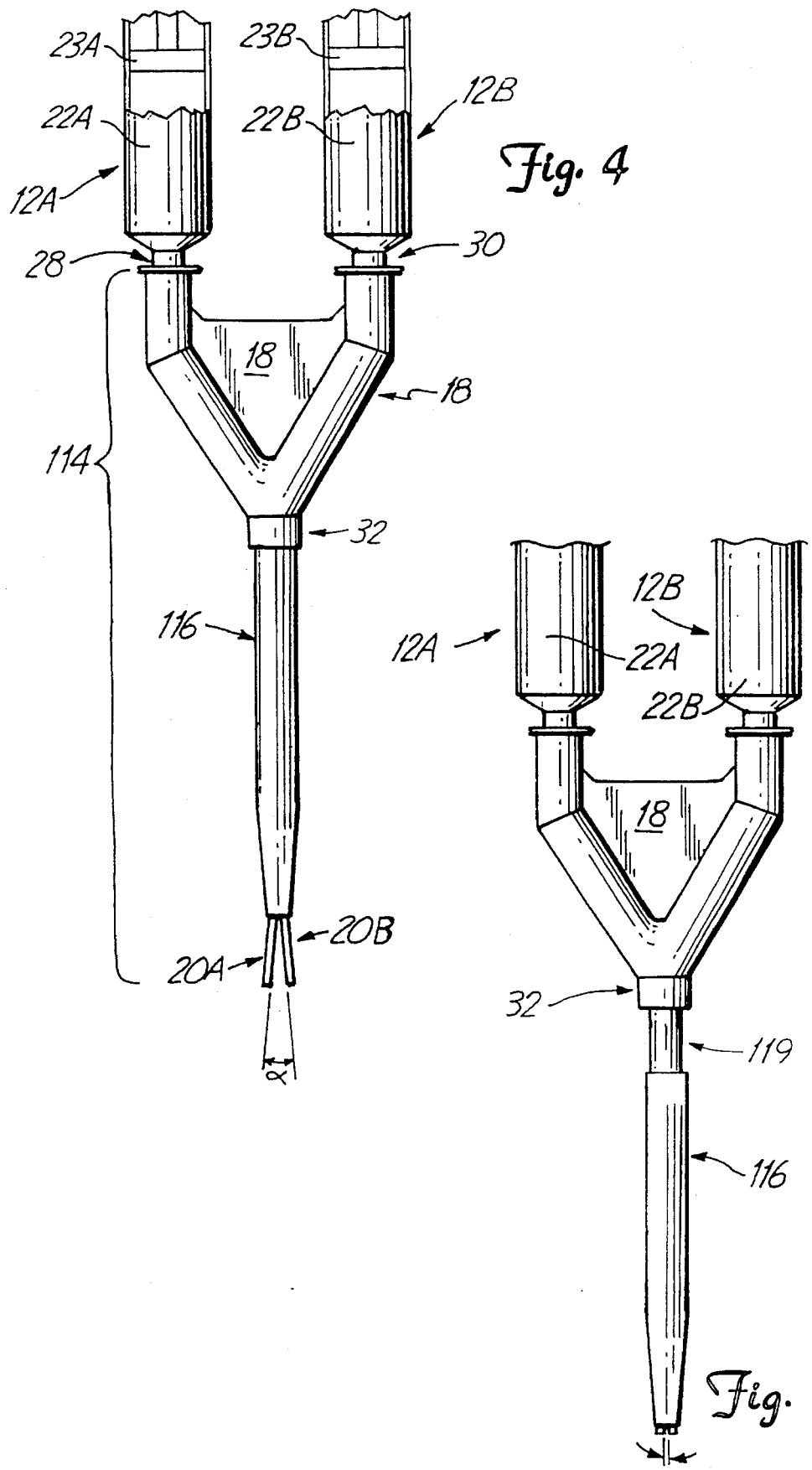

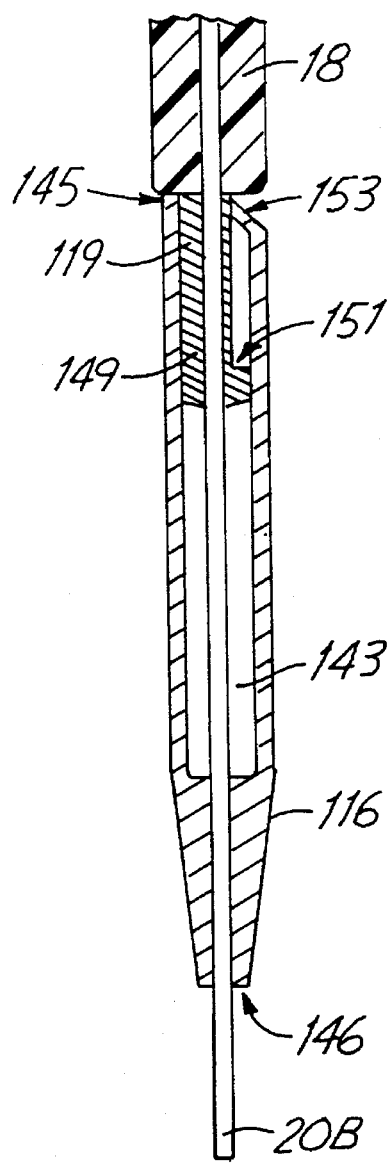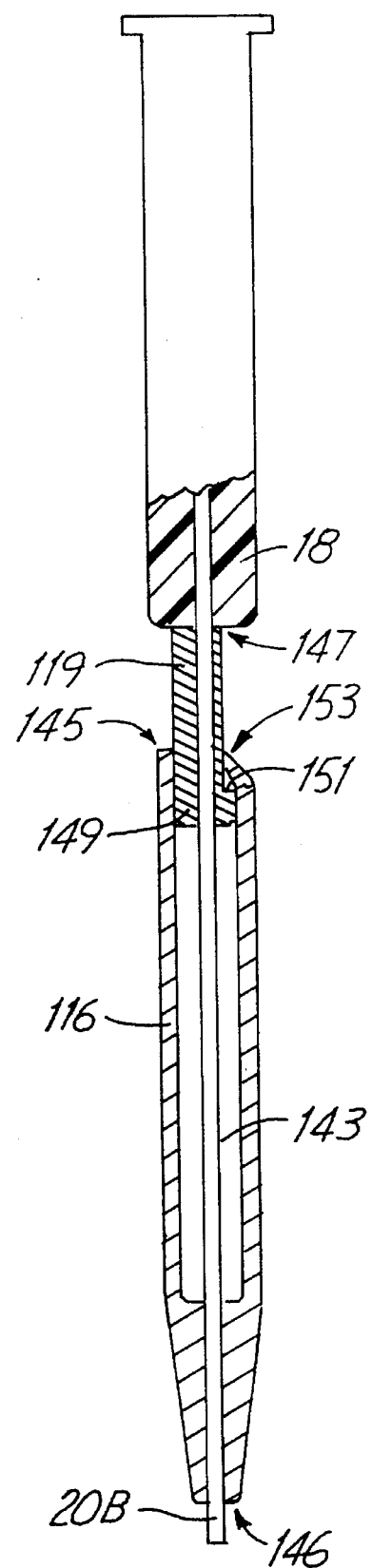
Fig. 7
Fig. 8

FLUID SEPARATION CONTROL ATTACHMENT FOR PHYSIOLOGIC GLUE APPLICATOR

BACKGROUND OF THE INVENTION

This invention relates generally to the design of an improved delivery system for applying adhesives. More particularly, the delivery system includes a pair of syringes, each with a plunger which when activated results in the combining of fluids in the syringes. The fluids, which are stored separately, are applied to a surface such as a treatment site as a stream. Although useful for any adhesive made from at least one solution, the delivery system is useful for combining tissue adhesive components such as a first solution of fibrinogen and a second solution of thrombin. Upon contact with one another, these two solutions undergo a rapid chemical reaction which causes coagulation into a functional tissue adhesive. Thus, it is desired to keep these two solutions separately confined until just prior to the time of direct application on a patient and then thoroughly and rapidly mix them for treatment of a wound.

The treatment of wounds on patients typically involves suturing or covering the wound with an external dressing. There are some applications, however, where the external dressing or sutures are not effective or even act as an irritant. In situations such as treatment of internal body cavities, it has been discovered that treatment of the wound with the body's own healing compounds has been very effective in inducing wound closure and subsequent healing. A common method of treating these wounds takes advantage of the rapid reaction which occurs when a solution of clotting factors, such as fibrinogen, comes into contact with a solution of a catalyst, such as thrombin, to form a complex which acts as a tissue adhesive. This rapid reaction typically commences within a few seconds after the solutions initially contact one another, and it typically attains a soft set after several more seconds of contact. A common name for such a complex is fibrin glue.

These fibrin glues have been known in the medical field for many years. U.S. Pat. No. 2,533,004 which issued on Dec. 5, 1950 to John D. Ferry discloses mixing varying concentrations of fibrinogen with thrombin to create fibrin clots.

Typical fibrin glue delivery systems either externally or internally mix the fluids. Internal mixing generally takes place in a mixing chamber where the amount of time the mixed solution remains in the mixing chamber is minimized. This minimization must occur so that the fibrin glue does not set up or coagulate within the mixing chamber and result in clogging of the chamber.

An internal mixing chamber is disclosed in U.S. Pat. No. 4,978,336, issued on Dec. 18, 1990 to Capozzi, et al. The syringe system of U.S. Pat. No. 4,978,336 has first and second syringes containing proteins which when mixed become a tissue adhesive. A manifold locks onto the two syringes. The manifold receives the output stream from each syringe and delivers the streams to an output nose. Detachably locked onto the output nose is a needle or spray nozzle. Mixing of the proteins either occurs within the lumen of the needle or within a mixing space provided within the output nose. The mixed combination is ejected from the either the needle or a spray outlet on the output nose resulting in application of the mixture to a wound.

Numerous devices with similar mixing chambers are known in the art. However, these devices typically all present similar problems. One of the problems is if the syringe plungers are depressed at a very slow rate, the reacting mixture is not evacuated from the system quickly enough and clotting can occur within the output nose or needle or within the mixing chamber. Thus, it has been found that for quick reacting substances, such as fibrin glue components, it is desired to have a method for uniform mixing that is not dependent on the rate at which the user introduces the solutions into the mixing chamber.

An additional problem which is characteristic of mixing chamber systems in which mixing occurs within the device is that this rapid reaction, once started, can coagulate backwards or upstream through the entire system and into at least one of the syringes containing the solutions of clotting factors. Thus, forward flow through the device must exceed the rate at which the reaction can coagulate backwards or upstream. Unless the user has been made aware that this can occur, he may be unaware of the minimum rate at which he should depress the syringes to counteract this tendency.

A number of devices exist which mix the components outside of the device thereby eliminating clotting within the mixing chamber. These devices typically use overlapping contact of airborne sprays or streams to obtain mixing. The apparatus utilized typically includes a fibrinogen solution stored separately from a thrombin solution, where these two solutions are mixed either immediately prior to or upon application on a wound, but in either case external to the device.

An example of a delivery system based on the mixing of overlapping jets of airborne particles is provided in U.S. Pat. No. 4,874,368, which was issued on Oct. 17, 1989 to Miller, et al. The delivery system disclosed in U.S. Pat. No. 4,874,368 provides a two syringe apparatus which enables the two solutions to stream from a sprayer and mix upon application over a wound. A connecting clip member is fitted on each of the piston-type plungers inserted into each syringe. The tip of each syringe is fitted with a specially formed needle, bent to receive the initially parallel outflow from each syringe. The bend in each needle redirects the outflow through a hollow plastic sleeve which serves as a retainer for the long, parallel needle tips. These tips extend slightly beyond the distal end of the hollow sleeve. As solution exits each tip, it is propelled into a spray or stream. The trajectories of the sprays partially overlap and begin mixing either while airborne or as they strike the surface being treated. The clotting reaction commences as the solutions contact one another. The close positioning of the needle tips to each other may result in spray from one tip coming to rest at the orifice of the other tip, which if the apparatus is temporarily not being used by the surgeon, may result in the clotting reaction proceeding upstream into the confines of the needle. This will result in the system being plugged and any further use of the device typically being prohibited.

It is accordingly a principle object of the present invention to provide a new and improved fluid delivery system which permits rapid and complete blending of two solutions thereby resulting in the formation of fibrin glue while prohibits clotting within the delivery system when the system is temporarily not being used by the surgeon.

SUMMARY OF THE INVENTION

This invention is a fluid delivery device for applying adhesives, particularly fluid components which combine to create fibrin glue type adhesives, where clotting of the device is avoided. The device applies to a treatment site a first and a second fluid, which when mixed, transform to a solid state, typically by the process of clotting.

The fluid delivery device has a pair of syringes connected to a fluid separation control attachment. The pair of syringes separately store the fluid components. A pair of tubes extend through the fluid separation control attachment. The tubes are fixed at one end by the fluid separation control attachment. The other end of each of the tubes is a free end. One of the syringes is connected to the fixed end of one of the tubes, and the other syringe is connected to the fixed end of the other tube.

A slidable sleeve has two ducts therein, and is slid onto the free end of each of the tubes. The slidable sleeve is shorter in length than the free portion of the tubes, i.e., the portion not fixed by the fluid separation control attachment. The slidable sleeve is slidable on the free portion of the tubes from a first position where one end of the slidable sleeve touches the fluid separation control attachment to a second position where the other end of the slidable sleeve is adjacent the free end of the tubes.

Each of the tubes has a bend in the free portion of the tube. When the bends are within the ducts of the slidable sleeve is in its second position, while when the bends are not within the ducts of the slidable sleeve is in its first position. The free ends of each of the tubes, when the sleeve is in its second position, direct the bends in an oblique manner so that any fluid dispensed therefrom or remaining thereon will not interact with fluid dispensed from or remaining on the free end of the other tube. When the free ends of each of the tubes are forced into the ducts (which occurs when the sleeve is in the first position) the bends are temporarily straightened.

When the medical professional, which is typically a surgeon, determines that wound closure is needed the plungers in each of the syringes are depressed. This results in at least some of the fluid within the syringes being forced into the tubes. The fluid travels through the tubes and is dispensed out of their free ends. The surgeon would typically only want to depress the plungers when the slidable sleeve is in the second position. The dispensed fluids would then mix on or about the treatment site and form a fibrin glue.

After the surgeon has dispensed a selected amount of fluids, the surgeon will discontinue depressing the plungers and typically set the fluid delivery device aside. During this temporary period of non-use, while the surgeon is continuing the surgical process or closure thereof, that spray overlap or dripping from the tubes will co-mingle when the tubes are in close proximity to one another. This co-mingling of fluids may result in the contamination of at least one of the tube ends or the internal confines of one of the tubes by fluid from the other tube, thereby resulting in coagulation of the fluids. This coagulation will eventually cause the tube to become plugged.

Since the tubes in many situations must be in close proximity to each other for proper mixing to occur, the tubes need to be separable only during non-use of the device. To avoid this contamination and plugging, the surgeon when using the fluid delivery device of the present invention can slide the slidable sleeve from the second position to the first position when the device is not in use. This results in the separation of the tube ends such that contamination is unlikely to occur.

DESCRIPTION OF THE DRAWINGS

FIG. 1 shows a top view of the fluid separation control attachment with its sleeve in a first position whereby the fluid outlets are separated;

FIG. 2 shows a top view of the fluid separation control attachment with its sleeve in a second position whereby the fluid outlets are in close proximity;

FIG. 4 shows a top view of a second embodiment of the fluid separation control attachment with its sleeve in a first position whereby the fluid outlets are separated, where the attachment contains a stop;

FIG. 5 shows a top view of the fluid separation control attachment with its sleeve in a second position whereby the fluid outlets are in close proximity, where the attachment contains a stop;

FIG. 7 shows a side view of a second embodiment of the fluid separation control attachment with its sleeve in a first position whereby the fluid outlets are separated, where the attachment contains a stop;

FIG. 8 shows a side view of a second embodiment of the fluid separation control attachment with its sleeve in a second position whereby the fluid outlets are in close proximity, where the attachment contains a stop.

While the above identified drawing features set forth preferred embodiments, this disclosure presents illustrative embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DESCRIPTION OF THE PREFERRED EMBODIMENT

A fluid separation device 10 for delivery of fluid components of fibrin glue to a treatment site is shown in FIG. 1. Fluid separation device 10 comprises a first and second syringe 12A and 12B, and a fluid separation control attachment 14. Fluid separation control attachment 14 includes a slidable sleeve 16, a Y-shaped manifold 18, and first and second tubes 20A and 20B partially therein.

Figure 3:
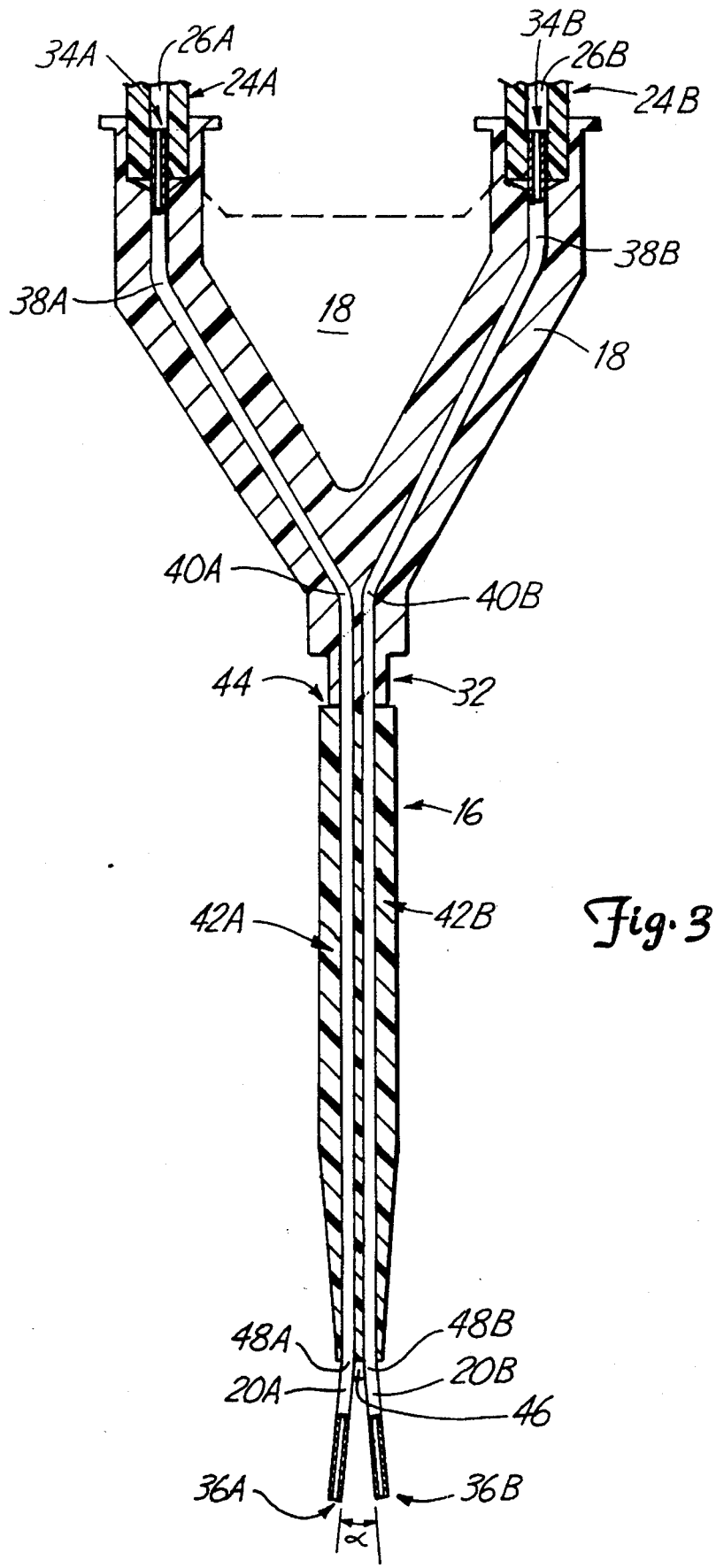
FIG. 3 shows a sectional view of the fluid separation control attachment with its sleeve in the first position.
Figure 6:
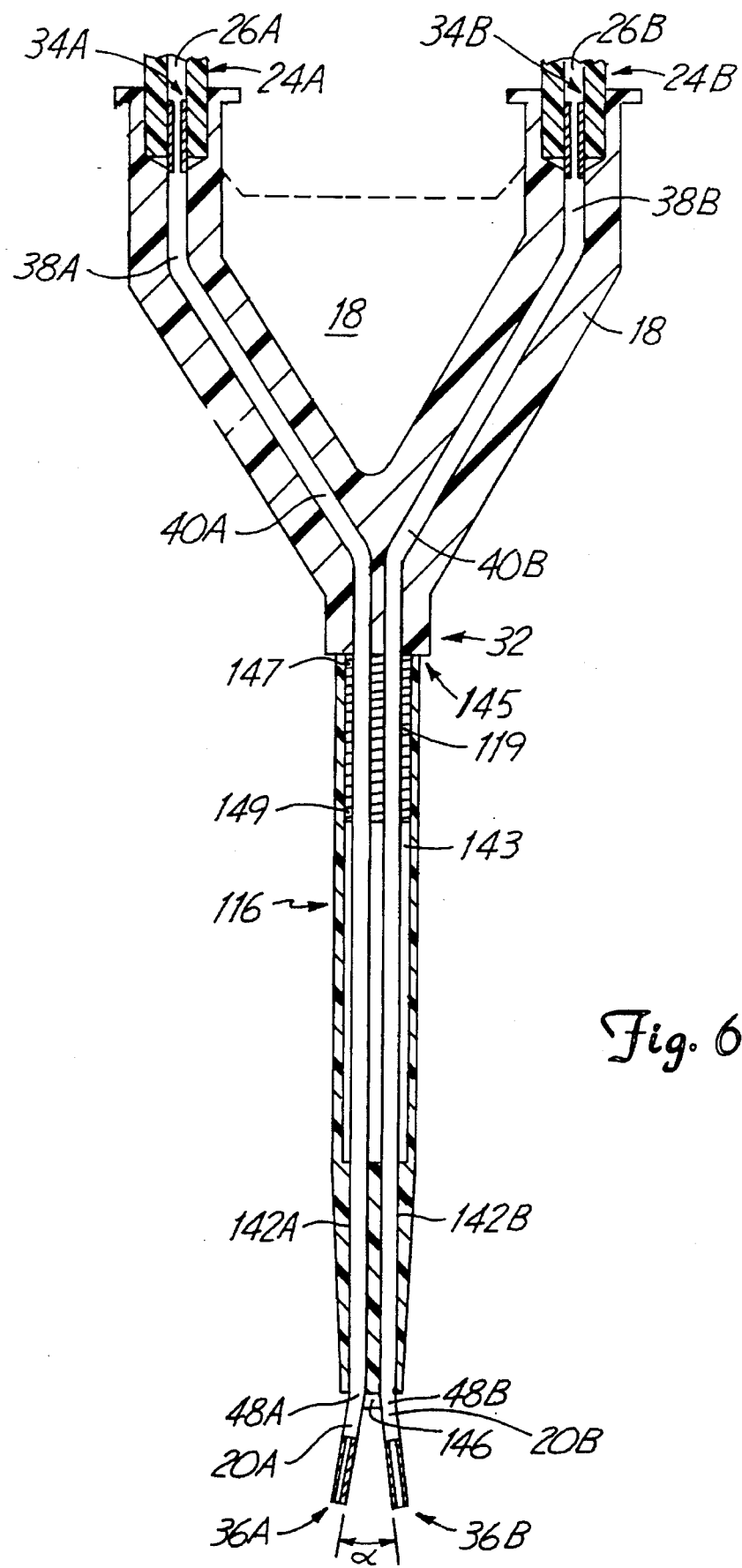
FIG. 6 shows a sectional view of the fluid separation control attachment with its sleeve in the first position, where the attachment contains a stop.

First and second syringes 12A and 12B are conventional syringes. Syringe 12A, although not fully shown in the figures has a cylinder 22A, a plunger 23A, and a tip 24A with a syringe outlet 26A (as shown in FIG. 3) therein. Syringe 12B is of identical construction to syringe 12A and corresponding elements are correspondingly numbered.

Cylinder 22A is for holding a fluid. When plunger 23A, which is in contact with the fluid in cylinder 22A, moves toward tip 24A the fluid in cylinder 22A is dispensed through the syringe outlet 26A.

Cylinder 22B is for holding a fluid. When plunger 23B, which is in contact with the fluid in cylinder 22B, moves toward tip 24B, the fluid in cylinder 22B is dispensed through the syringe outlet 26B. Typically, plungers 23A and 23B will be moved simultaneously so that some quantity of each fluid is dispensed out of both syringe outlets 26A and 26B to be mixed together. However, situations may arise where it is necessary to dispense only one fluid at a time, or dispense the fluids at varying rates in comparison to each other. The dispensing of fluids from each of the syringes at different or varying rates may be accomplished either by moving the plungers in same size syringes at differing rates or moving the plungers in differing size syringes at the same rates.

Fluid separation control attachment 14 includes Y-shaped manifold 18. Manifold 18 has first and second manifold inlets 28 and 30, and a manifold outlet 32. First and second manifold inlets 28 and 30 are countersunk into manifold 18. Manifold inlets 28 and 30 may be designed to receive conventional Luer-lock connectors. One skilled in the art will readily appreciate that manifold inlets 28 and 30 may be designed to receive any tapered connectors as well as other similar male-female connectors will work equally as well for many applications.

Manifold 18 will typically be made of a polymer. Tubes 20A and 20B will typically be made of a metal such as stainless steel. Manifold 18 is molded about a portion of first and second tubes 20A and 20B. Tube 20A extends through manifold 18 from first manifold inlet 28 to manifold outlet 32. Tube 20B extends through manifold 18 from second manifold inlet 30 to manifold outlet 32. First tube 20A has a first end 34A and a second end 36A. Second tube 20B has a first end 34B and a second end 36B. First end 34A extends slightly out of the countersunk first manifold inlet 28 such that when tip 24A is seated in inlet 28, first end 34A of first tube 20A is inserted into syringe outlet 26A. First end 34B extends slightly out of the countersunk second manifold inlet 30 such that when tip 24B is seated in inlet 30, first end 34B of second tube 20B is inserted into syringe outlet 26B. The seating of tips 24A and 24B into manifold inlets 28 and 30 results in a sealed fit which prohibits fluid leakage.

Manifold 18 has a first tube 20A molded therein with a first bend 38A and a second bend 40A. Manifold 18 has second tube 20B molded therein with a first bend 38B and a second bend 40B. Second bends 40A and 40B align tubes 20A and 20B such that the tubes extend adjacent to each other from the second bends to second ends 36A and 36B with the exception of third bends 48A and 48B (which are discussed later in detail).

Slidable sleeve 16 includes first and second parallel lumens or ducts 42A and 42B. However, it is contemplated that only one duct be provided in slidable sleeve 16 to receive both tubes 20A and 20B. Slidable sleeve 16 is slid over a portion of tubes 20A and 20B that extends out from manifold 18 such that the tubes are inserted into ducts 42A and 42B, respectively. Slidable sleeve 16 has a first sleeve end 44 and a second sleeve end 46. First sleeve end 44 rests against manifold 18 and is in a first position when slidable sleeve 16 is inserted on tubes 28 and 30 as far as possible. This first position is shown in FIGS. 1 and 3.

First and second tubes 20A and 20B each include a third bend 48A and 48B, respectively. Third bends 48A and 48B are located on tubes 20A and 20B, respectively between second sleeve end 46 and second ends 36A and 36B. Third bends 48A and 48B skew the direction of second ends 36A and 36B so that the fluids dispensed from tubes 20A and 20B do not intersect. Specifically, when slidable sleeve 16 is in its first position (shown in FIGS. 1 and 3), the second ends 36A and 36B are oriented at an angle α, as seen in FIG. 3.

When the slidable sleeve 16 is in its first position the tubes 20A and 20B are directed in a skewed or oblique manner so that the fluid dispensation paths from second ends 36A and 36B do not intersect. As such, the second ends 36A and 36B are separated by a distance sufficient to prohibit residual or dripping fluid from one tube from interact is with residual or dripping fluid from the other tube. In practice, only one third bend is needed to separate second ends 36A and 36B such that interaction between residual or dripping fluids is prevented.

Sleeve 16 is slidable over tubes 20A and 20B from its first position (FIG. 1) to a second position (FIG. 2). Tubes 20A and 20B are sufficiently flexible and elastic such that slidable sleeve 16 may be slid from the first position to a second position (FIG. 2) away from manifold 1 8 and thus over third bends 48A and 48B. This results in the alignment of the free second ends 36A and 36B to a generally parallel, closely-spaced arrangement such that the fluid dispensed from the ends 36A and 36B of the tubes 20A and 20B will intersect and react with each other to form fibrin glue. When slidable sleeve 16 is in its second position, second ends 36A and 36B are either adjacently touching or maximally spaced apart a distance which allows for the fluids dispensed from tubes 20A and 20B to interact with each other and form fibrin glue, preferably on a treatment site.

Tubes 20A and 20B are sufficiently elastic such that third bends 48A and 48B deflect, and thus straighten, when slidable sleeve 16 is slid from its second position to its first position. However, tubes 20A and 20B are sufficiently inelastic such that any bend therein (such as third bends 48A and 48B) will deflect back to the original bend angle α when slidable sleeve 16 is slid back into its first position from its second position.

Alternatively, slidable sleeve 16 may have a core of deflectable material surrounded by a polymer cover. The core of deflectable material, through which ducts 42A and 42B extend, allows the third bend to be forced into each of the ducts since the deflectable material gives thereby increasing the diameter of the duct and allowing the bend access. The polymer cover is rigid and will hold slidable sleeve 16 together during any deflection in the core.

Slidable sleeve 16 is simple to use. When a medical professional, such as a surgeon, during a medical procedure, such as a surgery needs to induce wound closure and healing, the surgeon forces plungers 23A and 23B downward in cylinders 22A and 22B such that the fluid in the cylinders flows into the separate tubes 20A and 20B. Continued pressure on the plungers when slidable sleeve 14 is its second position results in dispensing of the fluid in the cylinders through second ends 36A and 36B.

When a sufficient amount of fibrin glue has formed, the surgeon removes the force from plungers 23A and 23B thereby stopping the dispensing of the fluids. The surgeon then slides slidable sleeve 16 from its second position (FIG. 2) to its first position (FIG. 1). The surgeon can generally perform the step of sliding simultaneously or within a very minimal time before or after removing the force from the plungers. This assures that the residual or dripping fluid from one of the second ends 36A and 36B does not contaminate the other end, which would result in clotting in or about the end of fluid separation device 10.

When the surgeon is again ready to induce wound closure and healing, slidable sleeve 16 is slid from its first position to its second position. These steps of sliding slidable sleeve 16 from its first position to its second position are repeated as many times as necessary during a surgical procedure. The result is that only one fluid separation device is needed during a surgery since clogging of the apparatus is prevented.

Alternative designs of the fluid separation control attachment (which result in the second ends being adjusted back and forth from the first position to the second position such that the tubes do not become plugged from coagulation due to contamination of one tube from the fluid of the other tube) have been contemplated and are within the scope of this invention. One alternative design has a pair of parallel flexible tubes which are initially positioned in a first position as described above. A tube separation mechanism separates the tubes by bending them away from each other into second position as described above.

In FIGS. 4–8, an alternative embodiment for a control attachment for the delivery of fluid components of fibrin glue is shown. In this embodiment, the control attachment includes a stop for preventing the slidable sleeve from sliding completely off of the tubes. The stop also prevents the tubes from being withdrawn completely from the sleeve.

FIGS. 4–5 show a fluid separation control attachment 114 attached to conventional syringes 12A and 12B which have been previously described. Fluid separation control attachment 114 includes an alternative slidable sleeve 116, Y-shaped manifold 18, a sleeve stop 119, and first and second tubes 20A and 20B.

Slidable sleeve 116 has a first end 145 and a second end 146. Slidable sleeve 116 includes first and second parallel lumens or ducts 142A and 142B extending from second end 146 into the slidable sleeve 116. Ducts 142A and 142B enlarge in size at a mid-portion in slidable sleeve 116 to form an internal cavity 143 (see FIG. 6). Internal cavity 143 extends from first end 145 of slidable sleeve 116 into the slidable sleeve 116 where it connects with ducts 142A and 142B. Ducts 142A and 142B will align or skew tubes 20A and 20B as in the other embodiment, while internal cavity 143 allows sleeve stop 119 to function as explained below.

Sleeve stop 119 has a first end 147 that is connected to manifold 18 about manifold outlet 32. Sleeve stop 119 has a second end 149 (spaced from the manifold 18) which includes an outwardly extending protrusion or ridge 151, as shown in FIGS. 7–8, such that the second end has a larger cross sectional area than first end 147.

Sleeve stop 119 is slidably positioned within internal cavity 143. This allows slidable sleeve 116 to slide on sleeve stop 119 and first and second tubes 20A and 20B from a first position adjacent manifold outlet 32 (FIG. 4) to a second position away from manifold outlet 32 (FIG. 5) where the second position is defined by the distance ridge 151 allows slidable sleeve 116 to slide. As described above in detail for slidable sleeve 16, when slidable sleeve 116 is in its first position the tubes 20A and 20B are directed in a skewed or oblique manner so that the fluid dispensation paths from second ends 36A and 36B do not intersect. As such, the second ends 36A and 36B are separated by a distance sufficient to prohibit residual or dripping fluid from one tube from interact is with residual or dripping fluid from the other tube. When slidable sleeve 116 is in its second position, end portions of the tubes 20A and 20B are covered by the slidable sleeve 116 and within ducts 142A and 142B, respectively. As such, second ends 36A and 36B are either adjacently touching or maximally spaced apart a distance which allows for the fluids dispensed from tubes 20A and 20B to interact with each other and form fibrin glue, preferably on a treatment site.

At its first end 145, slidable sleeve 116 has an inwardly extending inner lip or ridge 153. Ridge 153 engages ridge 151 when slidable sleeve 116 is slid away from the manifold 118, as shown in FIGS. 5 and 8 (when ridge 153 engages ridge 151, slidable sleeve 116 is in its second position). Slidable sleeve 116 is thus limited from sliding any further away from the manifold 118 by the engagement of ridges 151 and 153. This prevents slidable sleeve 116 from sliding completely off of tubes 20A and 20B. The catching action also may be used to prevent second ends 36A and 36B from being withdrawn completely into slidable sleeve 116.

In sum, the invention is a fluid mixing and delivery device for use during surgery where clotting of the dispensing tubes is avoided. A tube aligning mechanism such as the slidable sleeve is used to align the free ends of the tubes during fluid dispensation while separating the tubes when no fluid dispensation is occurring to prevent fluid contact between the free ends since such fluid contact may result in contamination or clotting.

Although the present invention has been described with reference to preferred embodiments, workers skilled in the art will recognize that changes may be made in form and detail without departing from the spirit and scope of the invention.

What is claimed is:

1. A fluid separation control attachment for use in combination with first and second reservoirs for simultaneously applying first and second fluids to a treatment site, the fluids being stored in the first and second reservoirs respectively and kept separate from each other until dispensed onto the treatment site, the first and second reservoirs having first and second outlets, respectively, through which the fluids in each reservoir are dispensed under pressure, the fluid separation control attachment comprising:

a first tube having a first end and a second end, the first tube being connectable at its first end to the first outlet;

a second tube having a first end and a second end, the second tube being connectable at its first end to the second outlet; and a tube end aligning mechanism for selectively moving the second ends of the tubes between a first position wherein the second ends are spaced apart and a second position wherein the second ends are adjacent, the tube end aligning mechanism being disposed between the first and second ends of the tubes, wherein when in the first position, the second ends of the first and second tubes are aligned to avoid mixing of the fluids dispensed therefrom, and wherein when in the second position, the second ends of the first and second tubes are aligned to enhance mixing of the fluids dispensed therefrom.

2. The fluid separation control attachment of claim 1 wherein the tube end aligning mechanism comprises a slidable sleeve having at least one duct therein for receiving the tubes, the duct in the slidable sleeve being slidably positioned on the tubes, wherein the slidable sleeve is slidable back and forth from the first position to the second position.

3. The fluid separation control attachment of claim 2 wherein the first position comprises the second end of the first tube being oblique to the second end of the second tube such that any fluid dispensed from one of the tubes is prevented from interacting with any fluid dispensed from the other tube, and wherein the second position comprises the second end of the first tube being substantially parallel to the second end of the second tube such that any fluid dispensed from each of the tubes interacts resulting in the two fluids reverting to a solid state.

4. The fluid separation control attachment of claim 1 further comprising a Y-shaped body through which at least a portion of each of the first and second tubes extend.

5. The fluid separation control attachment of claim 2 wherein the slidable sleeve contains a stop mechanism for preventing sliding of the slidable sleeve on the tubes beyond the second ends of the tubes.

6. A fluid separation apparatus for applying to a treatment site a first fluid and a second fluid, the fluid separation apparatus comprising:

a first fluid reservoir for storing the first fluid, the first fluid reservoir having a first outlet for dispensing the first fluid under pressure;

a second fluid reservoir for storing the second fluid, the second fluid reservoir having a second outlet for dispensing the second fluid under pressure, where the fluids are kept separate from each other until dispensed onto the treatment site;

a first tube having a first and second end, the first tube being connected at its first end to the first outlet;

a second tube having a first and second end, the second tube being connected at its first end to the second outlet;

a tube end aligning mechanism for selectively moving the second ends of the tubes between a first position wherein the second ends are adjacent and a second position wherein the second ends are spaced apart, the tube end aligning mechanism being disposed between the first and second ends of the tubes, wherein when in the first position, the second ends of the first and second tubes are aligned to avoid mixing of the fluids dispensed therefrom, while when in the second position, the second ends of the first and second tubes are aligned to enhance mixing of the fluids dispensed therefrom.

7. The fluid separation apparatus of claim 6 wherein the tube end aligning mechanism comprises a slidable sleeve having at least one duct therein for receiving the tubes, the duct in the slidable sleeve being slidably positioned on the tubes, wherein the slidable sleeve is slidable back and forth from the first position to the second position.

8. The fluid separation apparatus of claim 7 wherein the first position comprises the second end of the first tube being oblique to the second end of the second tube such that any fluid dispensed from one of the tubes is prevented from interacting with any fluid dispensed from the other tube, and wherein the second position comprises the second end of the first tube being substantially parallel to the second end of the second tube such that any fluid dispensed from each of the tubes interacts resulting in the two fluids reverting to a solid state.

9. The fluid separation apparatus of claim 6 further comprising a Y-shaped body through which at least a portion of each of the first and second tubes extend.

10. The fluid separation apparatus of claim 6 wherein the first fluid reservoir is a syringe, the syringe having a first cylinder for containing the first fluid, a first plunger which is movable in the first cylinder, and the first outlet through which the first fluid is delivered by movement of the first plunger within the first cylinder.

11. The fluid separation apparatus of claim 10 wherein the second fluid reservoir is a syringe, the syringe having a second cylinder for containing the second fluid, a second plunger which is movable in the second cylinder, and the second outlet through which the second fluid is delivered by movement of the second plunger within the second cylinder.

12. The fluid separation apparatus in claim 6 further comprising a first fluid stored in the first reservoir and a second fluid stored in the second reservoir wherein the first fluid is a fibrinogen, and the second fluid is a thrombin.

13. The fluid separation control attachment of claim 7 wherein the slidable sleeve contains a stop mechanism for preventing sliding of the slidable sleeve on the tubes beyond the second ends of the tubes.

14. A fluid separation control attachment for use in combination with first and second reservoirs for simultaneously applying first and second fluids to a treatment site, the fluids being stored in the first and second reservoirs respectively and kept separate from each other until dispensed onto the treatment site, the first and second reservoirs having first and second outlets, respectively, through which the fluids in each reservoir are dispensed under pressure, the fluid separation control attachment comprising:

a first tube having a first end and a second end, the first tube being connected at its first end to the first outlet;

a second tube having a first end and a second end, the second tube being connected at its first end to the second outlet; and a tube end aligning mechanism for selectively moving the second ends of the tubes between a first position wherein the second ends are spaced apart and a second position wherein the second ends are adjacent, the tube end aligning mechanism comprising a slidable sleeve having at least one duct therein for receiving the tubes, the duct in the slidable sleeve being slidably positioned on the tubes, wherein the slidable sleeve is slidable back and forth from the first position to the second position, wherein when in the first position, the second ends of the first and second tubes are aligned to avoid mixing of the fluids dispensed therefrom, and wherein when in the second position, the second ends of the first and second tubes are aligned to enhance mixing of the fluids dispensed therefrom.

15. A fluid separation control attachment for use in combination with first and second reservoirs for simultaneously applying first and second fluids to a treatment site, the fluids being stored in the first and second reservoirs respectively and kept separate from each other until dispensed onto the treatment site, the first and second reservoirs having first and second outlets, respectively, through which the fluids in each reservoir are dispensed under pressure, the fluid separation control attachment comprising:

a first tube having a first end and a second end, the first tube being connected at its first end to the first outlet and having a first bend between the first and second end of the first tube;

a second tube having a first end and a second end, the second tube being connected at its first end to the second outlet and having a second bend between the first and second end of the second tube; and a tube end aligning mechanism for selectively moving the second ends of the tubes between a first position wherein the second ends are spaced apart and a second position wherein the second ends are adjacent, the first and second tubes being sufficiently elastic to straighten when the second ends are in the second position while being sufficiently inelastic such that the bends therein deflect back when the second ends are in the first position, wherein when in the first position, the second ends of the first and second tubes are aligned to avoid mixing of the fluids dispensed therefrom, and wherein when in the second position, the second ends of the first and second tubes are aligned to enhance mixing of the fluids dispensed therefrom.

16. A fluid separation control attachment for use in combination with first and second reservoirs for simultaneously applying first and second fluids to a treatment site, the fluids being stored in the first and second reservoirs respectively and kept separate from each other until dispensed onto the treatment site, the first and second reservoirs having first and second outlets, respectively, through which the fluids in each reservoir are dispensed under pressure, the fluid separation control attachment comprising:

a first tube having a first end and a second end, the first tube being connected at its first end to the first outlet;

a second tube having a first end and a second end, the second tube being connected at its first end to the second outlet;

a Y-shaped body through which at least a portion of each of the first and second tubes extend; and a tube end aligning mechanism for selectively moving the second ends of the tubes between a first position wherein the second ends are spaced apart and a second position wherein the second ends are adjacent, wherein when in the first position, the second ends of the first and second tubes are aligned to avoid mixing of the fluids dispensed therefrom, and wherein when in the second position, the second ends of the first and second tubes are aligned to enhance mixing of the fluids dispensed therefrom.

17. A fluid separation apparatus for applying to a treatment site a first fluid and a second fluid, the fluid separation apparatus comprising:

a first fluid reservoir for storing the first fluid, the first fluid reservoir having a first outlet for dispensing the first fluid under pressure;

a second fluid reservoir for storing the second fluid, the second fluid reservoir having a second outlet for dispensing the second fluid under pressure, where the fluids are kept separate from each other until dispensed onto the treatment site;

a first tube having a first and second end, the first tube being connected at its first end to the first outlet and having a first bend between the first and second end of the first tube;

a second tube having a first and second end, the second tube being connected at its first end to the second outlet and having a second bend between the first and second end of the second tube; and a tube end aligning mechanism for selectively moving the second ends of the tubes between a first position wherein the second ends are adjacent and a second position wherein the second ends are spaced apart, the tubes are sufficiently elastic to straighten when the second ends are in the second position while being sufficiently inelastic such that the bends therein deflect back when the second ends are in the first position, wherein when in the first position, the second ends of the first and second tubes are aligned to avoid mixing of the fluids dispensed therefrom, while when in the second position, the second ends of the first and second tubes are aligned to enhance mixing of the fluids dispensed therefrom.

18. A fluid separation apparatus for applying to a treatment site a first fluid and a second fluid, the fluid separation apparatus comprising:

a first fluid reservoir for storing the first fluid, the first fluid reservoir having a first outlet for dispensing the first fluid under pressure;

a second fluid reservoir for storing the second fluid, the second fluid reservoir having a second outlet for dispensing the second fluid under pressure, where the fluids are kept separate from each other until dispensed onto the treatment site;

a first tube having a first and second end, the first tube being connected at its first end to the first outlet;

a second tube having a first and second end, the second tube being connected at its first end to the second outlet; and a tube end aligning mechanism for selectively moving the second ends of the tubes between a first position wherein the second ends are adjacent and a second position wherein the second ends are spaced apart, the end aligning mechanism comprising a slidable sleeve having at least one duct therein for receiving the tubes, the duct in the slidable sleeve being slidably positioned on the tubes, wherein the slidable sleeve is slidable back and forth from the first position to the second position, wherein when in the first position, the second ends of the first and second tubes are aligned to avoid mixing of the fluids dispensed therefrom, while when in the second position, the second ends of the first and second tubes are aligned to enhance mixing of the fluids dispensed therefrom.

19. A fluid separation apparatus for applying to a treatment site a first fluid and a second fluid, the fluid separation apparatus comprising:

a first fluid reservoir for storing the first fluid, the first fluid reservoir having a first outlet for dispensing the first fluid under pressure;

a second fluid reservoir for storing the second fluid, the second fluid reservoir having a second outlet for dispensing the second fluid under pressure, where the fluids are kept separate from each other until dispensed onto the treatment site;

a first tube having a first and second end, the first tube being connected at its first end to the first outlet;

a second tube having a first and second end, the second tube being connected at its first end to the second outlet;

a Y-shaped body through which at least a portion of each of the first and second tubes extend; and a tube end aligning mechanism for selectively moving the second ends of the tubes between a first position wherein the second ends are adjacent and a second position wherein the second ends are spaced apart, wherein when in the first position, the second ends of the first and second tubes are aligned to avoid mixing of the fluids dispensed therefrom, while when in the second position, the second ends of the first and second tubes are aligned to enhance mixing of the fluids dispensed therefrom.

20. A fluid separation apparatus for applying to a treatment site a first fluid and a second fluid, the fluid separation apparatus comprising:

a first fluid reservoir for storing the first fluid, the first fluid reservoir having a first outlet for dispensing the first fluid under pressure;

a second fluid reservoir for storing the second fluid, the second fluid reservoir having a second outlet for dispensing the second fluid under pressure, where the fluids are kept separate from each other until dispensed onto the treatment site;

a first fluid stored in the first reservoir and a second fluid stored in the second reservoir wherein the first fluid is a fibrinogen, and the second fluid is a thrombin;

a first tube having a first and second end, the first tube being connected at its first end to the first outlet;

a second tube having a first and second end, the second tube being connected at its first end to the second outlet; and a tube end aligning mechanism for selectively moving the second ends of the tubes between a first position wherein the second ends are adjacent and a second position wherein the second ends are spaced apart, wherein when in the first position, the second ends of the first and second tubes are aligned to avoid mixing of the fluids dispensed therefrom, while when in the second position, the second ends of the first and second tubes are aligned to enhance mixing of the fluids dispensed therefrom.

* * * * *